(12) United States Patent
Wollenberg et al.

(10) Patent No.: US 7,256,161 B2
(45) Date of Patent: Aug. 14, 2007

(54) PROCESS FOR MAKING GROUP II METAL CARBONATED, OVERBASED MANNICH CONDENSATION PRODUCTS OF ALKYLPHENOLS

(75) Inventors: Robert H. Wollenberg, Orinda, CA (US); Jeremy Cantor, Benicia, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 504 days.

(21) Appl. No.: 10/713,948

(22) Filed: Nov. 13, 2003

(65) Prior Publication Data

US 2005/0107266 A1    May 19, 2005

(51) Int. Cl.
*C10M 159/16* (2006.01)
*C10M 125/10* (2006.01)
*C10L 1/22* (2006.01)

(52) U.S. Cl. .................. 508/222; 508/542; 508/545

(58) Field of Classification Search ............... 508/222, 508/542, 545
See application file for complete search history.

(56) References Cited

U.S. PATENT DOCUMENTS

| | | | |
|---|---|---|---|
| 3,036,003 A | 5/1962 | Verdol | |
| 3,340,190 A | 9/1967 | Deluga et al. | |
| 3,372,118 A * | 3/1968 | Rense | 508/542 |
| 3,586,629 A | 6/1971 | Otto et al. | |
| 3,798,163 A | 3/1974 | Palmer | |
| 3,958,624 A | 5/1976 | Peeler et al. | |
| 4,025,316 A | 5/1977 | Stover | |
| 4,088,586 A | 5/1978 | Wilgus et al. | |
| 4,131,551 A * | 12/1978 | Thompson et al. | 508/209 |
| 4,140,492 A | 2/1979 | Feldman et al. | |
| 4,157,308 A | 6/1979 | Wilgus et al. | |
| 4,218,328 A * | 8/1980 | Vaughan | 508/287 |
| 4,219,430 A | 8/1980 | Vaughan | |
| 4,231,759 A | 11/1980 | Udelhofen et al. | |
| 4,435,273 A | 3/1984 | Ferm et al. | |
| 4,655,949 A | 4/1987 | Landry et al. | |
| 4,717,492 A | 1/1988 | Chibnik | |
| 4,734,211 A | 3/1988 | Kennedy | |
| 4,764,296 A | 8/1988 | Kennedy | |
| 4,803,002 A * | 2/1989 | Wollenberg | 508/194 |
| 4,806,130 A | 2/1989 | Chibnik | |
| 4,820,432 A | 4/1989 | Lundberg et al. | |
| 5,173,203 A * | 12/1992 | Nichols et al. | 508/401 |
| 5,207,939 A * | 5/1993 | Farng et al. | 508/557 |
| 5,370,805 A * | 12/1994 | Smrcka et al. | 508/542 |
| 5,652,201 A * | 7/1997 | Papay et al. | 508/228 |

* cited by examiner

*Primary Examiner*—Callie Shosho
(74) *Attorney, Agent, or Firm*—Sarita R. Kelley

(57) ABSTRACT

This invention is directed to a novel process for making Group II metal carbonated, overbased Mannich condensation products of alkylphenols, which process uses ethylene carbonate as both a source of carbon dioxide and ethylene glycol. In particular, under the reaction conditions using ethylene carbonate in the present invention, carbonation and overbasing Mannich condensation products of alkylphenols is possible while at the same time the viscosity of the carbonated, overbased Mannich condensation products of alkylphenols remains within acceptable levels, typically under 1000 cSt at 100° C. The present invention is also directed to carbonation of Mannich condensation products of alkylphenols using a $C_2$-$C_6$ alkaline glycol and carbon dioxide. The present invention is also directed to a detergent-dispersant antioxidant additive composition comprising Group II metal carbonated, overbased Mannich condensation products of alkylphenols, wherein the Group II metal carbonated, overbased Mannich condensation products of alkylphenols have a $CO_2$ to Ca ratio of at least 0.01.

36 Claims, No Drawings

PROCESS FOR MAKING GROUP II METAL CARBONATED, OVERBASED MANNICH CONDENSATION PRODUCTS OF ALKYLPHENOLS

FIELD OF THE INVENTION

This invention is directed to a novel process for making Group II metal carbonated, overbased Mannich condensation products of alkylphenols, which process uses ethylene carbonate as both a source of carbon dioxide and ethylene glycol. In particular, under the reaction conditions using ethylene carbonate in the present invention, overbasing of Mannich condensation products of alkylphenols is possible while at the same time viscosity of the carbonated, overbased Mannich condensation products of alkylphenols remains within acceptable levels, typically under 1000 cSt at 100° C. This invention is also directed to a process for making Group II metal carbonated, overbased Mannich condensation products of alkylphenols, which process uses carbon dioxide and ethylene glycol. The present invention is also directed to a detergent-dispersant antioxidant additive composition comprising Group II metal carbonated, overbased Mannich condensation products of alkylphenols, wherein the Group II metal carbonated, overbased Mannich condensation products of alkylphenols have a $CO_2$ to Ca ratio of at least 0.01.

The present invention is also directed to a lubricating oil additive comprising Group II metal carbonated, overbased Mannich condensation products of alkylphenols, which is low in sulfur content, typically less than 0.3 percent as measured by ASTM Test No. D 4951-92.

The present invention is also directed to a Mannich condensation product comprising a reaction product of an alkylphenol, an aldehyde and N-phenyl-1,4-phenylene diamine.

BACKGROUND OF THE INVENTION

The operation of diesel and spark ignition internal combustion engines is typically accompanied by the formation of sludge, lacquer and resinous deposits which adhere to the moving engine parts and thereby reduce engine efficiency. In order to prevent or reduce the formation of these deposits, a wide variety of chemical additives have been developed for incorporation into lubricating oils. These additives are commonly referred to as detergents and dispersants. Dispersants have the ability to keep deposit forming materials suspended in the oil so as to retard deposit formation during engine operation. Detergents have the ability to remove pre-existing deposits from the engine during engine operation and to neutralize acids in railroad, marine and automotive engines.

A large number of railroad and tugboat diesel engines use silver-plated bearings. As a result, the lubricating oil requires acceptable silver wear control and corrosion performance in addition to deposit control and alkalinity. Mannich bases and their salts have been known to be effective to protect silver bearing parts in such engines without the disadvantages associated with the use of chlorinated and dithiophosphate additives.

Mannich bases and their salts are also known to be particularly useful in lubricating oils, fuels, greases and plastics as antioxidants. Hydrocarbon materials are highly susceptible to chemical action on aging, exposure to sunlight and in their normal use. Such oxidation can lead to the deposit of undesirable residues in lubricants, fuels and greases and to discoloration of plastics.

Frequently, the inclusion of additives in lubricating oils and fuels to control deposits, wear and oxidation cause compatibility problems. In addition, it is uneconomical to add many additives in order to achieve all these functions.

Thus, there is a great need for the development of a single multifunctional agent that will perform all these desired functions.

One class of lubricating oil additives typically used as dispersants, detergents, oxidation inhibitors and anti-wear additives are Mannich condensation products of an alkylphenol, an aldehyde and an amine.

Various Mannich condensation products known in the prior art as lubricating oil additives are metal salts. Currently, there is no carbonation process in the prior art for making Group II metal carbonated, overbased Mannich condensation products of alkylphenol which have a high alkalinity reserve for neutralizing acids in engines and at the same time have acceptable viscosity. It is believed that the carbonate, overbased Mannich condensation products of alkylphenols of the present invention are superior to the prior art salts of Mannich condensation products of alkylphenols for providing the functions of detergent-dispersants, anti-wear and oxidation agents in one additive because of their greater alkalinity reserve and acceptable viscosities.

The ability of additive compositions to neutralize acids in engines can be measured by determining the total base number (TBN) or the alkalinity reserve of the composition. Higher TBNs reflect a greater capacity for these compositions to neutralize acids generated during engine operation. However, the TBN of a composition is directly related to the amount of diluent oil present. Thus, more concentrated compositions will have a higher TBN than those containing more diluent.

The preparation of Group II metal salts of Mannich condensation products of alkylphenol compositions is well known in the art. A number of patents have discussed processes for making Group II metal salts of the Mannich condensation products of alkylphenols, but none have included a carbonation step in the process.

For example, U.S. Pat. No. 3,036,003 discloses a process for making a metal salt of a condensation product of an alkylene polyamine, an aldehyde and substituted phenol.

U.S. Pat. No. 3,340,190 discloses the preparation of a mixture of the exactly neutralized calcium salt of N,N'-bis (alkyl substituted hydroxybenzyl)alkylene diamine and a bis (alkenylsuccinimide) of polyalkylene polyamine or of a urea condensation derivative of polyalkylene polyamine, N,N'-bis(polyazalkylamino) ureylene.

U.S. Pat. No. 3,586,629 discloses the preparation of salts obtained by reacting the condensation product of an alkyl hydroxy aromatic compound, an aldehyde and an amine or alkali metal salt thereof with a metal base. These salts provide excellent detergency characteristics to an organic industrial fluid.

U.S. Pat. No. 3,798,163 teaches a method for inhibiting exhaust valve recession in natural gas fueled internal combustion engines with the use of composition comprising a lubricating oil, a metal sulfonate and at least one metal salt of a condensation product of an alkylene polyamine, an aldehyde and a substituted phenol.

U.S. Pat. No. 3,958,624 discloses an improved anti-fouling additive for use in organic heat transfer fluids comprising a combination of a barium overbased calcium sulfonate and a phenolic antioxidant, an alkaline earth aminophenate.

U.S. Pat. No. 4,025,316 discloses the preparation of polymeric alkyl-hydroxy benzyl N-substituted amines having a high degree of ring formation derived from the condensation reaction of $C_8$-$C_{40}$ aliphatic alkyl substituted hydroxy aromatic, an aldehyde and an amine.

U.S. Pat. No. 4,088,586 discloses the preparation of salts of Mannich bases from tetrapropenylphenol, formaldehyde and diethylenetriamine when the molar ratio of the reactant is 1 mole tertapropenylphenol to 0.5 to 0.85 mole formaldehyde to at least 0.3 mole of diethylenetriamine having outstanding viscosity and alkalinity value properties.

U.S. Pat. No. 4,140,492 discloses the preparation of borated derivatives of oil-soluble Mannich bases for use in combination with coadditive hydrocarbons for flow improvers for middle distillate fuel oils.

U.S. Pat. No. 4,157,308 discloses the preparation of Mannich base compositions and their metal salts from phenolic mixtures consisting of phenol alkylated with a propylene tetramer and phenol alkylated with a straight-chain alpha-olefin.

U.S. Pat. No. 4,231,759 discloses a liquid hydrocarbon combustion fuel containing an additive composition comprising the Mannich condensation product of a high molecular weight alkyl-substituted hydroxyaromatic compound wherein the alkyl group has a molecular weight of from about 600 to about 3,000.

U.S. Pat. No. 4,655,949 discloses novel lubricating oil composition comprising an organomettalic additive containing a metal selected from Groups I, Ib and VIII chelated with the reaction product of formaldehyde, an amino acid and a phenol.

U.S. Pat. Nos. 4,734,211; 4,764,296 and 4,820,432 disclose a lubricating oil composition for railway diesel engines which contains calcium salt of Mannich reaction product among other additives. The Mannich base is prepared using an alkyl substituted hydroxy aromatic compound, specifically para-alkyl phenol. The TBN of the product was approximately 160.

Typically, Mannich bases are prepared by reacting an alkylphenol with an aldehyde and an amine wherein the amine is a primary or secondary aliphatic or aromatic amine or polyamine, and the aldehyde is an aliphatic or aromatic aldehyde. The alkyl group of the phenol can be straight-chain or branched-chain. Optionally, a promoter may be used during the condensation reaction.

The prior art process for making the metal salt of the Mannich bases is typically by the addition of a metal oxide, hydroxide or hydroperoxide. Optionally, ethylene glycol is added to the reaction mixture to promote the salt formation.

SUMMARY OF THE INVENTION

The present invention is directed to a novel process for making Group II metal carbonated, overbased Mannich condensation products of alkylphenols, which process uses ethylene carbonate as both a source of carbon dioxide and ethylene glycol. In particular, under the reaction conditions using ethylene carbonate in the present invention, overbasing, as defined herein, of Mannich alkylphenols is possible while at the same time the viscosity of the carbonated, overbased Mannich condensation products of alkylphenols remains within acceptable levels, typically under 1000 cSt at 100° C. This invention is also directed to a process for making Group II metal carbonated, overbased Mannich condensation products of alkylphenols, which process uses carbon dioxide and ethylene glycol. The present invention is also directed to a detergent-dispersant antioxidant additive composition comprising Group II metal carbonated, overbased Mannich condensation products of alkylphenols, wherein the Group II metal carbonated, overbased Mannich condensation products of alkylphenols have a $CO_2$ to Ca ratio of at least 0.01.

The present invention is also directed to a lubricating oil additive comprising Group II metal carbonated, overbased Mannich condensation products of alkylphenols, which is low in sulfur content, typically less than 0.3 percent as measured by ASTM Test No. D 4951-92. It is believed that the sulfur content in the Group II metal carbonated, overbased Mannich condensation products of alkylphenols of the present invention is contributed by the diluent used in the preparation of the Group II metal carbonated, overbased Mannich condensation products of alkylphenols.

In particular, the process of the present invention for preparing Group II metal carbonated, overbased Mannich condensation products of alkylphenols comprises:

forming a reaction mixture by combining a Mannich condensation product of an alkylphenol wherein the alkyl group contains a sufficient number of carbon atoms to render oil-soluble the resulting Group II metal carbonated, overbased Mannich condensation product of alkylphenol, a Group II metal oxide, hydroxide or $C_1$-$C_6$ alkoxide, in the presence of a promoter and optionally a second promoter, and an alkylene carbonate selected from ethylene carbonate or a mono-alkyl or di-alkyl substituted ethylene carbonate, said alkylene carbonate having the following structure:

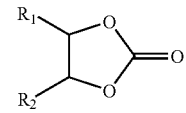

wherein $R_1$ and $R_2$ are independently hydrogen or alkyl containing one to three carbon atoms; and wherein the combining is carried out for a time and at a temperature sufficient to form in situ carbon dioxide and alkylene glycol, or a reacting equivalent, to form a product comprising a Group II metal carbonated, overbased Mannich condensation product of alkylphenol.

In the alkylene carbonate structure above, preferably one of $R_1$ and $R_2$ is hydrogen and the other is hydrogen or methyl. In other words, the alkylene carbonate is preferably ethylene carbonate or propylene carbonate. More preferably, $R_1$ and $R_2$ are both hydrogen; that is, the alkylene carbonate is ethylene carbonate.

In another embodiment, the Mannich condensation product of alkylphenol used in the process of the present invention as described above may be replaced with a Group II metal salt.

A further embodiment of the present invention is directed to a process for making Group II metal carbonated, overbased Mannich condensation products of alkylphenols, in which process a $C_2$-$C_{10}$ alkylene glycol and carbon dioxide replace the alkylene carbonate. Preferably, the $C_2$-$C_{10}$ alkylene glycol is ethylene glycol.

The alkylene carbonate is added to the reaction mixture over a time period of about 15 minutes to about 120 minutes. Preferably, the alkylene carbonate is added to the reaction mixture over a time period of about 30 minutes to about 90 minutes, and more preferably the alkylene carbonate is added to the reaction mixture over a time period of about 40 minutes to about 60 minutes.

The promoter used in the process of the present invention is typically a $C_2$-$C_{10}$ alkylene glycol.

The promoter optionally used in the process of the present invention may typically include water, a $C_1$-$C_5$ mono- or di-alcohol or a $C_2$-$C_{10}$ alkylene glycol or a mixture thereof. Preferably, the promoter optionally used is a $C_2$-$C_{10}$ alkylene glycol, and more preferably the promoter optionally used is water.

Optionally, the process of the present invention further comprises the step of recovering the product by filtering the reaction mixture to remove sediment.

An alternate embodiment of the present process for preparing Group II metal carbonated, overbased Mannich condensation products of alkylphenols comprises the steps of:
(a) forming a reaction mixture by combining a Mannich condensation product of alkylphenol wherein the alkyl group contains a sufficient number of carbon atoms to render oil-soluble the resulting Group II metal carbonated, overbased Mannich condensation product of alkylphenol, a Group II metal oxide, hydroxide or $C_1$-$C_6$ alkoxide, a promoter and optionally a second promoter; and
(b) contacting said reaction mixture with an alkylene carbonate selected from ethylene carbonate or a mono-alkyl or di-alkyl substituted ethylene carbonate, said alkylene carbonate having the following structure:

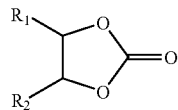

wherein $R_1$ and $R_2$ are independently hydrogen or alkyl containing one to three carbon atoms; and wherein the contacting is carried out for a time and at a temperature sufficient to form in situ carbon dioxide and alkylene glycol, or a reacting equivalent, to form a product comprising a Group II metal carbonated, overbased Mannich condensation product of alkylphenol.

In the alkylene carbonate structure above, preferably one of $R_1$ and $R_2$ is hydrogen and the other is hydrogen or methyl. In other words, the alkylene carbonate is preferably ethylene carbonate or propylene carbonate. More preferably, $R_1$ and $R_2$ are both hydrogen; that is, the alkylene carbonate is ethylene carbonate.

The Mannich condensation product of alkylphenol used in the alternate embodiment of the process of the present invention as described above may be replaced with a Group II metal salt.

A further embodiment of the alternate embodiment is directed to a process for making Group II metal carbonated, overbased Mannich condensation products of alkylphenols, in which process a $C_2$-$C_{10}$ alkylene glycol and carbon dioxide replace the alkylene carbonate in step (b). Preferably, the $C_2$-$C_{10}$ alkylene glycol is ethylene glycol.

The alkylene carbonate is added to the reaction mixture over a time period of about 15 minutes to about 120 minutes. Preferably, the alkylene carbonate is added to the reaction mixture over a time period of about 30 minutes to about 90 minutes, and more preferably the alkylene carbonate is added to the reaction mixture over a time period of about 40 minutes to about 60 minutes.

The promoter used in step (a) of the above process of the present invention is a $C_2$-$C_{10}$ alkylene glycol.

The promoter optionally used in step (a) of the process is typically water, a $C_1$-$C_5$ mono- or di-alcohol or a $C_2$-$C_{10}$ alkylene glycol or a mixture thereof. Preferably, the promoter optionally used is a $C_2$-$C_{10}$ alkylene glycol, and more preferably the promoter optionally used is water.

Optionally, the process of this embodiment further comprises the step of recovering the product by filtering the reaction mixture to remove sediment.

Another embodiment of the present process for preparing Group II metal carbonated, overbased Mannich condensation products of alkylphenols comprises the steps of:
(a) forming a first reaction mixture by combining an alkylphenol wherein the alkyl group contains a sufficient number of carbon atoms to render oil-soluble the resulting Group II metal carbonated, overbased Mannich condensation product of alkylphenol, an aldehyde and an amine and a promoter optionally used;
(b) contacting said first reaction mixture with a second reaction mixture comprising a Group II metal oxide, hydroxide or $C_1$-$C_6$ alkoxide; an inert hydrocarbon diluent, a promoter and optionally a second promoter to form a third reaction mixture; and
(c) contacting said third reaction mixture with an alkylene carbonate selected from ethylene carbonate or a mono-alkyl or di-alkyl substituted ethylene carbonate, said alkylene carbonate having the following structure:

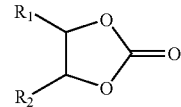

wherein $R_1$ and $R_2$ are independently hydrogen or alkyl containing one to three carbon atoms; and wherein said contacting is carried out for a time and at a temperature sufficient to form in situ carbon dioxide and alkylene glycol, or a reacting equivalent, to form a product comprising a Group II metal carbonated, overbased Mannich condensation product of alkylphenol.

In the alkylene carbonate structure above, preferably one of $R_1$ and $R_2$ is hydrogen and the other is hydrogen or methyl. In other words, the alkylene carbonate is preferably ethylene carbonate or propylene carbonate. More preferably, $R_1$ and $R_2$ are both hydrogen; that is, the alkylene carbonate is ethylene carbonate.

In step (a) of the above embodiment of the present invention, the temperature of reaction mixture is in the range of about 35° C. to about 170° C.

A further embodiment is directed to a process for making Group II metal carbonated, overbased Mannich condensation products of alkylphenols, in which process a $C_2$-$C_{10}$ alkylene glycol and carbon dioxide replace the alkylene carbonate in step (c). Preferably, the $C_2$-$C_{10}$ alkylene glycol is ethylene glycol.

The alkylene carbonate is added to the reaction mixture over a time period of about 15 minutes to about 120 minutes. Preferably, the alkylene carbonate is added to the reaction mixture over a time period of about 30 minutes to about 90 minutes, and more preferably the alkylene carbonate is added to the reaction mixture over a time period of about 40 minutes to about 60 minutes.

The promoter used in step (b) of the process of the above present embodiment is a $C_2$-$C_{10}$ alkylene glycol.

The promoter optionally used in step (b) of the above present embodiment is typically water, a $C_1$-$C_5$ mono- or di-alcohol or a $C_2$-$C_{10}$ alkylene glycol or a mixture thereof. Preferably, the promoter is a $C_2$-$C_{10}$ alkylene glycol, and more preferably the promoter is water.

In step (a), the amine may be an aliphatic amine, an aromatic amine, a polyfunctional amine, such as ethanol amine, or mixtures thereof, containing at least one amino group characterized by the presence of at least one active hydrogen or methylene group, and wherein the amine contains only primary amino groups, only secondary amino groups, or both primary and secondary amino groups.

The aliphatic amine may be an alkylene diamine, a dialkylamine, a polyalkylene polyamine or mixtures thereof. The aromatic amine may be a single-ring aromatic amine or a double-ring aromatic amine.

In step (a), the aldehyde may be an aliphatic aldehyde, aromatic aldehyde, a heterocyclic aldehyde or mixtures thereof. Preferably, the aliphatic aldehyde is formaldehyde or paraformaldehyde, the aromatic aldehyde is benzaldehyde, and the heterocyclic aldehyde is furfural.

The molar ratios of the alkylphenol, the aldehyde and the amine in step (a) are from about 1:1.8:1 to about 1:3:1.

The alkyl group of the alkylphenol may be straight-chain or branched-chain and will typically contain at least 10 carbon atoms, preferably from about 12 carbon atoms to about 50 carbon atoms.

Preferably, the alkyl group of the alkylphenol contains from about 25 to about 100 mole percent predominantly straight-chain alkyl groups containing from about 15 to about 35 carbon atoms and from about 75 to about 0 mole percent branched-chain alkyl groups containing from about 9 to about 18 carbon atoms. Preferably, the alkyl group of the alkylphenol contains from about 40 to about 70 mole percent predominantly straight-chain alkyl groups containing from about 15 to about 35 carbon atoms and from about 60 to about 30 mole percent branched-chain alkyl groups containing from about 9 to about 18 carbon atoms.

In a preferred embodiment, the alkyl group of the alkylphenol is attached predominantly at the para position of the phenol ring. Preferably, the alkylphenol containing the para attachment of the alkyl group is from about 70 to about 95 weight percent of the total alkylphenol. More preferably, the alkylphenol containing the para attachment of the alkyl group is from about 80 to about 95 weight percent of the total alkylphenol.

The Group II metal oxide, hydroxide or $C_1$-$C_6$ alkoxide is selected from the group consisting of calcium, barium, and magnesium oxide, hydroxide or $C_1$-$C_6$ alkoxide and mixtures thereof. Preferably, the Group II metal oxide, hydroxide or $C_1$-$C_6$ alkoxide is calcium hydroxide.

Optionally, the process of this embodiment further comprises the step of recovering the product by filtering the reaction mixture to remove sediment.

The carbonation processes of the instant invention are particularly useful for preparing Group II metal carbonated, overbased Mannich condensation products of alkylphenols possessing a $CO_2$ to Ca ratio of at least about 0.01, and preferably in the range of about 0.1 to about 0.6, and more preferably in the range of about 0.3 to about 0.5.

The processes of the present invention may be carried out in a batch or a continuous process. It is believed that small changes in pressure will have little effect on the carbonation process of the present invention.

The present invention is also directed to a detergent-dispersant-and antioxidant additive comprising Group II metal carbonated, overbased Mannich condensation products of alkylphenols, said additive having a $CO_2$ to Ca ratio of at least about 0.01, and preferably in the range of about 0.1 to about 0.6, and more preferably in the range of about 0.3 to about 0.5.

The detergent-dispersant antioxidant additive of the present invention comprises Group II metal carbonated, overbased Mannich condensation product of alkylphenol wherein the Mannich alkylphenol is a condensation product of an alkylphenol, an aldehyde and an aliphatic, an aromatic, a polyfunctional amine or mixtures thereof, said additive having a $CO_2$ to Ca ratio of at least about 0.01, and preferably in the range of about 0.1 to about 0.6, and more preferably in the range of about 0.3 to about 0.5.

The present invention is also directed to a Mannich condensation product comprising a reaction product of an alkylphenol, an aldehyde and N-phenyl-1,4-phenylene diamine wherein the alkyl group of the alkylphenol is a straight-chain alkyl group or branched-chain alkyl group containing from about 10 carbon atoms to about 50 carbon atoms. Preferably, the alkyl group of the alkylphenol has about 12 carbon atoms to about 24 carbon atoms. The aldehyde is an aliphatic aldehyde, aromatic aldehyde, a heterocyclic aldehyde or mixtures thereof. Preferably, the aliphatic aldehyde is paraformaldehyde or formaldehyde. More preferably, the alkyl group of the alkylphenol has about 12 carbon atoms, the aldehyde is paraformaldehyde, and the amine is N-phenyl-1,4-phenylene diamine in the Mannich condensation product of this invention.

DETAILED DESCRIPTION OF THE INVENTION

Definitions

As used herein, the following terms have the following meanings unless expressly stated to the contrary:

The term "alkoxide" means a compound which can be formed as the reaction product of an alcohol and a reactive metal.

The term "alkylene glycol" means an aliphatic diol having two hydroxy groups on adjacent carbon atoms.

The term "alkylphenol" means a phenol group having one or more alkyl substituents, at least one of which has a sufficient number of carbon atoms to impart oil solubility to the phenol.

The term "carbonated, overbased Mannich condensation products of alkylphenols" means the products obtained after carbonation and overbasing, as described in the process of the present invention, of Mannich bases prepared by reacting an alkylphenol with an aldehyde and an amine wherein the amine is a primary or secondary aliphatic or aromatic amine or polyamine, the aldehyde is an aliphatic or aromatic aldehyde.

Use of the term "ethylene carbonate" includes alkyl-substituted alkylene carbonate, such as propylene carbonate and the like.

The term "overbased" as used herein describes those Group II metal carbonated, overbased Mannich condensation products of alkylphenols in which the ratio of carbon dioxide to calcium is at least 0.01 and may be as high as 0.6.

The term "promoter" means a $C_2$-$C_{10}$ alkylene glycol capable of assisting in the carbonation step of the process of the present invention.

The term "promoter optionally used" means any polar chemical, such as water, a $C_1$-$C_5$ mono- or di-alcohol or ethylene glycol or a mixture thereof, that is capable of assisting in the process of the present invention.

The term "one or more promoters" means a promoter or a promoter optionally used as defined herein.

The term "reacting equivalent" means any material equivalent to ethylene glycol and carbon dioxide, such as the carbonic acid half ester.

Sulfur content was measured by ASTM Test No. D 4951-92.

The term "Total Base Number" or "TBN" refers to the amount of base equivalent to milligrams of KOH in one gram of sample. The TBN of a sample can be determined by ASTM Test No. D 2896 or any other similar procedure.

Calcium content of the carbonated, overbased Group II metal Mannich condensation products of alkylphenols was measured using the following procedure:

Samples of 0.5 grams to 2.0 grams placed in 8 milliliter vials with plastic-lined screw caps and diluted with a solution of ortho-xylene that contains 8% mineral oil, 340D, and a 50 ppm Ag internal standard element. Analysis is done using the Inductively Coupled Plasma in an Inductively Coupled Plasma Optical Emission Spectrometer. Results are reported as parts per million (w/w) or weight percent.

Carbon dioxide content of the carbonated, overbased Group II metal Mannich condensation products of alkylphenols was measured using the following procedure:

Approximately 100 mg of sample is weighed into a test tube and acidified with p-toluene sulfonic acid to release $CO_2$. The liberated gases are swept through several scrubbers to remove interfering species. The resultant gas stream is bubbled into a solution that contains mono-ethanol amine (MEA) and a pH sensitive indicator. The addition of $CO_2$ to the solution changes the pH, which changes the color of the indicator. The color change is sensed by a visible spectrophotometer, and a controlling coulometer generates hydroxyl ion at an electrode in the solution to bring the pH back to its original value. The titration charge is related back to the original amount of acid evolved carbon in the sample by means of Coulomb's law. The result is given as weight percent $CO_2$.

Kinematic viscosity of the carbonated, overbased Group II metal Mannich condensation products of alkylphenols was measured using the following modified ASTM Test No. D 445:

A portion (1-5 milliliters) of sample is loaded into a calibrated Zeitfuchs cross-arm viscometer. The sample and viscometer are brought to thermal equilibrium by immersion in a temperature-controlled bath. The sample level is brought to a mark on the viscometer. The sample is induced to flow by applying a small momentary pressure; after the flow has begun, the sample flows under gravity. The time is measured for the sample to flow between two marks on the viscometer. The time is related to the sample viscosity by means of the previously determined calibration constant. Results are reported as centistokes at 100° C.

Unless otherwise specified, all percentages are in weight percent and the pressure is atmospheric pressure.

It has been determined that the alkalinity reserve of the Group II metal Mannich alkylphenols can be increased by the addition of a carbonation step after the neutralization of the Group II metal Mannich condensation products of alkylphenols with calcium hydroxide. The term "overbased" as used herein describes those Group II metal Mannich condensation products of alkylphenols in which the ratio of carbon dioxide to calcium is at least 0.01 and may be as high as 0.6. In contrast, the equivalent ratio of carbon dioxide to calcium is 0.0 in uncarbonated Group II metal Mannich condensation products of alkylphenol because the neutralization of Group II metal Mannich condensation products of alkylphenol is generally carried out with calcium hydroxide and without carbonation.

Without being bound by any theory, it is believed that one possible chemical structure of the Group II metal carbonated-overbased product of the carbonation step is as depicted below:

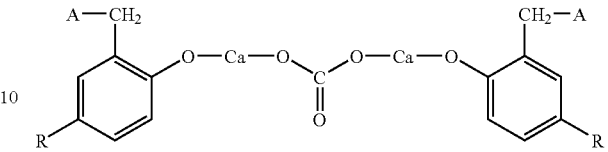

wherein R is alkyl and A is an amine or a polyamine.

Current automotive formulations require very low sulfur levels, less than 0.3 percent, and future formulations may require even lower levels of sulfur. Thus, the additive itself must add little or no sulfur to the finished lubricating oil product. However, conventional detergent-dispersant additives, such as Group II metal overbased sulfurized alkylphenols, increase the sulfur content of the finished lubricating oil product because of the high sulfur content of the additive. The carbonated, overbased Mannich condensation products of alkylphenol additives of the present invention have the distinct advantage over the conventional detergent-dispersant additives in that the final sulfur content of the additives is below 0.3 percent, which sulfur content may be present in the diluent oil used for making the carbonated, overbased Mannich condensation products of alkylphenols. The carbonated, overbased Mannich condensation products of alkylphenols themselves do not contain sulfur.

As noted above, this invention is directed to a novel process for the rapid carbonation of Mannich condensation products of alkylphenols using ethylene carbonate or alkylene-substituted ethylene carbonate. We have discovered that the ethylene carbonate in the carbonation step for the preparation of carbonated, overbased Mannich condensation products of alkylphenols can be used as both a source of carbon dioxide and ethylene glycol. Under the reaction conditions using ethylene carbonate, rapid carbonation of Mannich condensation products of alkylphenols is feasible for the preparation of carbonated, overbased Mannich condensation products of alkylphenols which has not been possible in the prior art processes.

The carbonation of Mannich condensation products of alkylphenols using the processes of the present invention provide a product with good alkalinity reserve and acceptable viscosity compared to the prior art salts of Mannich condensation products of alkylphenols without any loss in the quality of the product. The chemical and physical properties of the product of the present process are also good, including high base content, low crude product sediment and fast filtration rates.

EXAMPLES

General Procedure for Examples

Preparation of Carbonated, Overbased Mannich Condensation Products of Alkylphenols Below is described the procedure generally used for the preparation of carbonated, overbased Mannich condensation products of alkylphenols in accordance with the present invention. Specific amounts used in the preparation of Examples 1-46 and A-E are given in Tables I and VI.

Into a 4 liter, 5-neck resin kettle reactor equipped with metal baffle insert, a turbine blade mechanical stirrer and a reflux condenser (closed at the top), the following components were combined:

- 804.8 grams of $C_{10}$-$C_{15}$ alkylphenol
- 7.5 grams of defoamer, polydimethylsiloxane, Dow Corning 200® purchased from Dow Corning
- 168.2 grams of paraformaldehyde
- 480.8 grams of 150 Neutral oil purchased from ExxonMobil, which contained 0.278 and 0.374 percent sulfur.

The contents of the reactor were stirred to 600 rpm and the temperature was ramped to 50° C. and 88.4 grams of monomethylamine was added over a period of ½ hour. The temperature was ramped to 70° C. to 95° C. over the next 1 hour, cooling being employed if necessary to keep the temperature below 95° C. Next, the temperature was ramped to 140° C. for ½ hour, and then held at 140° C. for ½ hour. At the end of this time period, the vacuum was broken with air and 244.4 grams of 150 Neutral oil, which contained 0.278 and 0.374 percent sulfur, was added to the reactor. The reactor was cooled from 80° C. to 90° C., and the following additional components were added to the reactor:

- 213.6 grams of calcium hydroxide
- 18.8 grams of water

The temperature of the reactor was ramped to 120° C. while pressure was reduced to 500 mm Hg. The vacuum was broken with air and 58.6 grams of ethylene glycol was added to the reaction mixture over ½ hour. Pressure was gradually reduced to 500 mm Hg over next ½ hour, while holding the temperature at 120° C.

The temperature was ramped to 160° C. over the next 1 hour. The vacuum was then broken with nitrogen gas and ethylene carbonate was added to the reaction mixture over ½ hour.

Next, the temperature was ramped to 200° C. while maximum vacuum was applied to the reactor. The temperature was maintained at 200° C. for ½ hour.

Next, the vacuum was broken with nitrogen gas and 233.2 grams of 150 Neutral oil was added to the reaction mixture and mixed.

The product was collected after filtration with the addition of a filtration aid.

Examples 1-46

Preparation of Carbonated, Overbased Mannich Condensation Products of Alkylphenols Examples 1-46 were conducted using the procedure described above, except that the amine added to the reaction mixture in Examples 1-29 was a single amine while Examples 30-46 were conducted using a combination of two amines. Components kept constant in Test Examples 1-46 were the Charge Mole Ratios of paraformaldehyde at 1.942, of $Ca(OH)_2$ at 0.899, and of water at 0.362.

Table I below lists the components that were varied in Examples 1-29.

TABLE I

Amount of Reaction Components
Charge Mole Ratio relative to the Alkylphenol

| Ex. | Diethylenetriamine | Ethanol-amine | Monomethyl-amine | 1,4-Phenylene-diamine | N,phenyl-1,4-phenylene-diamine | Ethylene Glycol | Ethylene Carbonate |
|---|---|---|---|---|---|---|---|
| 1 | — | — | 0.987 | — | — | 0.328 | 0.394 |
| 2 | — | — | 0.987 | — | — | 0.328 | 0.453 |
| 3 | — | — | 0.914 | — | — | 0.298 | 0.358 |
| 4 | — | — | 0.942 | — | — | 0.284 | 0.358 |
| 5 | — | — | 0.970 | — | — | 0.284 | 0.358 |
| 6 | — | — | 0.987 | — | — | 0.328 | 0.634 |
| 7 | — | — | 0.987 | — | — | 0.328 | 0.634 |
| 8 | 1.000 | — | — | — | — | 0.328 | 0.394 |
| 9 | 1.000 | — | — | — | — | 0.328 | 1.000 |
| 10 | 1.000 | — | — | — | — | 0.328 | 0.697 |
| 11 | 1.000 | — | — | — | — | 0.328 | 1.000 |
| 12 | 0.667 | — | — | — | — | 0.328 | 0.667 |
| 13 | 0.495 | — | — | — | — | 0.328 | 1.304 |
| 14 | — | 0.997 | — | 0.499 | — | 0.328 | 0.394 |
| 15 | — | 0.997 | — | — | — | 0.284 | 0.358 |
| 16 | — | 1.047 | — | — | — | 0.284 | 0.358 |
| 17 | — | 1.047 | — | — | — | 0.284 | 0.358 |
| 18 | — | 1.047 | — | — | — | 0.284 | 0.376 |
| 19 | — | 1.047 | — | — | — | 0.284 | 0.376 |
| 20 | — | 1.047 | — | — | — | 0.284 | 0.376 |
| 21 | — | 1.152 | — | — | — | 0.284 | 0.376 |
| 22 | — | 1.204 | — | — | — | 0.284 | 0.376 |
| 23 | — | 1.256 | — | — | — | 0.284 | 0.376 |
| 24 | — | 1.047 | — | — | — | 0.284 | 0.376 |
| 25 | — | 1.047 | — | — | — | 0.284 | 0.395 |
| 26 | — | 1.047 | — | — | — | 0.284 | 0.413 |
| 27 | — | 1.047 | — | — | — | 0.284 | 0.434 |
| 28 | — | 1.047 | — | — | — | 0.284 | 0.456 |
| 29 | — | — | — | — | 1.000 | 0.284 | 0.413 |

The results obtained for Examples 1-29 are given below in Tables II to V.

Table II shows the results obtained when monomethyl amine was used to make the Mannich bases.

TABLE II

| Ex. | $CO_2/Ca$ | TBN | Sulfur (weight %) | Viscosity (cSt at 100° C.) | Sediment (volume %) |
|---|---|---|---|---|---|
| 1 | 0.394 | 159 | 0.21 | 154 | NA * |
| 2 | 0.425 | 188 | 0.17 | 219 | 12.0 |
| 3 | 0.424 | 200 | 0.20 | 402 | 3.6 |
| 4 | 0.350 | 196 | 0.16 | 551 | 4.8 |
| 5 | 0.342 | 207 | 0.17 | 693 | 1.4 |
| 6 | 0.422 | 186 | 0.20 | 103 | 4.0 |
| 7 | 0.492 | 180 | 0.14 | 214 | 10.0 |

* Data are not available.

Table III shows the results obtained when diethylenetriamine was used to make the Mannich bases.

TABLE III

| Ex. | $CO_2/Ca$ | TBN | Sulfur (weight %) | Viscosity (cSt at 100° C.) | Sediment (volume %) |
|---|---|---|---|---|---|
| 8 | 0.316 | 258 | 0.18 | 302 | 11.0 |
| 9 | NA * | 252 | 0.20 | 609 | 14.0 |
| 10 | 0.310 | 221 | 0.16 | 1181 | 14.0 |
| 11 | 0.336 | 200 | 0.19 | 599 | 1.3 |
| 12 | 0.489 | 155 | 0.16 | 251 | 16.0 |

* Data are not available.

Table IV shows the results obtained when ethanol amine was used to make the Mannich bases. No data were obtained for Example 13 because the product was too solid.

TABLE IV

| Ex. | $CO_2/Ca$ | TBN | Sulfur (weight %) | Viscosity (cSt at 100° C.) | Sediment (volume %) |
|---|---|---|---|---|---|
| 14 | 0.436 | 208 | 0.64 | 852 | 0.8 |
| 15 | 0.347 | 216 | 0.16 | 1103 | 1.5 |
| 16 | 0.390 | 214 | 0.17 | 1374 | 0.8 |
| 17 | 0.385 | 211 | 0.15 | 1282 | 2.2 |
| 18 | 0.374 | 208 | 0.13 | 748 | 0.5 |
| 19 | 0.401 | 209 | <0.05 | 721 | 0.5 |
| 20 | 0.392 | 199 | 0.13 | 685 | 1.2 |
| 21 | 0.384 | 209 | 0.15 | 831 | 0.3 |
| 22 | 0.400 | 207 | <0.12 | 1042 | 0.3 |
| 23 | 0.385 | 205 | <0.04 | 917 | 0.3 |
| 24 | 0.382 | 195 | 0.19 | 331 | 0.8 |
| 25 | 0.390 | 200 | 0.19 | 525 | 0.9 |
| 26 | 0.413 | 196 | 0.13 | 403 | 4.0 |
| 27 | 0.369 | 197 | 0.16 | 349 | 6.8 |
| 28 | 0.369 | 197 | 0.16 | 349 | 6.8 |

Table V shows the results obtained when N-phenyl,1,4-phenylene diamine was used to make the Mannich bases.

TABLE V

| Ex. | $CO_2/Ca$ | TBN | Sulfur (weight %) | Viscosity (cSt at 100° C.) | Sediment (volume %) |
|---|---|---|---|---|---|
| 29 | 0.144 | 87 | 0.10 | 374 | 8.0 |

Table VI below lists the components that were varied in Examples 30-46.

50 grams of alkylbenzene sulfonate, wherein the alkyl group on the benzene is 80 percent straight-chain $C_{20}$-$C_{24}$ and 20 percent branched-chain $C_{10}$-$C_{15}$, was added to the reaction mixture in Examples 35, 36, 38, 39 and 45. Ethylene glycol was not added to Example 45.

TABLE VI

Amount of Reaction Components
Charge Mole Ratio relative to the Alkylphenol

| Ex. | Diethylenetriamine | Ethanol-amine | Monomethyl-amine | 1,4-Phenylene-diamine | N,phenyl-1,4-phenylene-diamine | Ethylene Glycol | Ethylene Carbonate |
|---|---|---|---|---|---|---|---|
| 30 | — | — | 0.969 | 0.030 | — | 0.328 | 0.394 |
| 31 | — | — | 0.938 | 0.050 | — | 0.328 | 0.473 |
| 32 | — | — | 0.969 | 0.030 | — | 0.328 | 0.315 |
| 33 | — | — | 0.969 | 0.030 | — | 0.328 | 0.473 |
| 34 | — | — | 0.969 | 0.030 | — | 0.328 | 0.474 |
| 35 | — | — | 1.001 | 0.030 | — | 0.328 | 0.474 |
| 36 | — | — | 1.001 | 0.030 | — | 0.298 | 0.358 |
| 37 | — | — | 0.882 | 0.027 | — | 0.298 | 0.358 |
| 38 | — | — | 0.914 | 0.027 | — | 0.298 | 0.358 |
| 39 | — | — | 0.914 | 0.027 | — | 0.298 | 0.358 |
| 40 | — | 0.915 | — | 0.027 | — | 0.298 | 0.376 |
| 41 | — | 0.915 | — | 0.027 | — | 0.298 | 0.376 |
| 42 | — | 0.961 | — | 0.027 | — | 0.284 | 0.358 |
| 43 | — | 0.915 | — | 0.026 | — | 0.284 | 0.358 |
| 44 | — | 0.870 | — | 0.023 | — | 0.258 | 0.358 |
| 45 | — | 1.001 | — | 0.030 | — | 0.000 | 0.358 |
| 46 | — | 0.915 | — | 0.027 | — | 0.284 | 0.358 |

The results obtained in the above Examples 30-46 in Table VI are given below in Tables VII and VIII.

Table VII shows the results obtained when a combination of two amines, monomethyl amine and 1,4-phenylene diamine, was used to make the Mannich bases.

TABLE VII

| Ex. | $CO_2$/Ca | TBN | Sulfur (weight %) | Viscosity (cSt at 100° C.) | Sediment (volume %) |
|---|---|---|---|---|---|
| 30 | 0.413 | 194 | 0.19 | 307 | 5.6 |
| 31 | 0.425 | 176 | 0.17 | 175 | 6.0 |
| 32 | 0.411 | 186 | NA * | 284 | 8.4 |
| 33 | NA * | 152 | 0.23 | 117 | 9.2 |
| 34 | 0.397 | 154 | 0.19 | 100 | NA * |
| 35 | 0.446 | 160 | 0.23 | 89 | 12.3 |
| 36 | 0.414 | 171 | 0.27 | 113 | NA * |
| 37 | 0.455 | 197 | 0.23 | 502 | 3.2 |
| 38 | 0.450 | 193 | 0.26 | NA * | 3.2 |
| 39 | 0.454 | 190 | <0.06 | 178 | 5.0 |

* Data are not available.

Table VIII shows the results obtained when a combination of two amines, ethanol amine and 1,4-phenylene diamine, was used to make the Mannich bases.

TABLE VIII

| Ex. | $CO_2$/Ca | TBN | Sulfur (weight %) | Viscosity (cSt at 100° C.) | Sediment (volume %) |
|---|---|---|---|---|---|
| 40 | 0.437 | 183 | 0.25 | 573 | NA * |
| 41 | 0.356 | 190 | 0.08 | 681 | 5.6 |
| 42 | 0.347 | 196 | 0.07 | 947 | 2.4 |
| 43 | 0.323 | 203 | 0.05 | 926 | 2.4 |
| 44 | 0.349 | 195 | 0.19 | 967 | 2.2 |

TABLE VIII-continued

| Ex. | $CO_2$/Ca | TBN | Sulfur (weight %) | Viscosity (cSt at 100° C.) | Sediment (volume %) |
|---|---|---|---|---|---|
| 44 | 0.386 | 195 | 0.0 | 966 | 4.0 |
| 45 | 0.385 | 102 | 0.21 | 59 | 10.4 |
| 46 | 0.350 | 201 | 0.00 | 589 | 4.0 |

* Data are not available.

Examples A-E

The Preparation of Carbonated, Overbased Mannich Condensation Products of Alkylphenols using Ethylene Glycol and Carbon Dioxide Examples A-E experiments were conducted using the same procedure as used for Examples 30-46 above, except the ethylene carbonate was replaced with ethylene glycol and carbon dioxide for the carbonation of Mannich condensation products of alkylphenols. Components kept constant in Examples A-E were the Charge Mole Ratio of paraformaldehyde at 1.942, of $Ca(OH)_2$ at 0.899, and of water at 0.362. Ethylene glycol was added over a period of ½ hour and the carbon dioxide was added over a period of 1 hour.

In Examples A-D, 50 grams of alkylbenzene sulfonate, wherein the alkyl group on the benzene is 80 percent straight-chain $C_{20}$-$C_{24}$ and 20 percent branched-chain $C_{10}$-$C_{15}$ was added to the reaction mixture.

Table A below shows the components used in Examples A-E.

TABLE A

Amount of Reaction Components
Charge Mole Ratio relative to the Alkylphenol

| Ex. | Diethylenetriamine | Ethanol-amine | Monomethyl-amine | 1,4-Phenylene-diamine | N-phenyl-1,4-phenylene-diamine | Ethylene Glycol | $CO_2$ |
|---|---|---|---|---|---|---|---|
| A | — | — | — | 0.027 | — | 0.238 | 0.655 |
| B | — | — | 1.001 | 0.060 | — | 0.238 | 0.818 |
| C | — | — | 0.969 | 0.030 | — | 0.328 | 0.788 |
| D | — | — | 0.969 | 0.030 | — | 0.328 | 0.788 |
| E | — | — | 0.882 | 0.027 | — | 0.656 | 0.358 |

The results obtained for Examples A-E are given below in Table B.

TABLE B

| Ex. | $CO_2$/Ca | TBN | Sulfur (weight %) | Viscosity (cSt at 100° C.) | Sediment (volume %) |
|---|---|---|---|---|---|
| A | 0.480 | 134 | 0.29 | 78 | NA * |
| B | 0.600 | 130 | 0.17 | 88 | NA * |
| C | 0.375 | 140 | 0.29 | 162 | 8.0 |
| D | 0.564 | 149 | 0.26 | 235 | 7.2 |
| E | 0.456 | 198 | 0.31 | 434 | 7.2 |

* Data are not available.

What is claimed is:

1. A process for preparing Group II metal carbonated, overbased Mannich condensation products of alkylphenols which comprises:

forming a reaction mixture by combining a Mannich condensation product of an alkylphenol wherein the alkyl group contains a sufficient number of carbon atoms to render oil-soluble the resulting Group II metal carbonated, overbased Mannich condensation products of alkylphenol, a Group II metal oxide, hydroxide or $C_1$-$C_6$ alkoxide, one or more promoters, and an alkylene carbonate selected from ethylene carbonate or a mono-alkyl or di-alkyl substituted ethylene carbonate, said alkylene carbonate having the following structure:

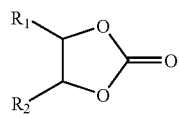

wherein $R_1$ and $R_2$ are independently hydrogen or alkyl containing one to three carbon atoms; and wherein the combining is carried out for a time and at a temperature sufficient to form in situ carbon dioxide and alkylene glycol, to form a product comprising a Group II metal carbonated, overbased Mannich condensation product of an alkylphenol, wherein the promoter comprises a $C_2$-$C_{10}$ alkylene glycol, and a second promoter, which is different from the first promoter, comprises water, a $C_1$-$C_5$ mono- or di-alcohol, ethylene glycol or a mixture thereof, and wherein the alkylene carbonate is added to the reaction mixture over a time period of about 15 minutes to about 120 minutes.

2. The process of claim 1 wherein the Mannich condensation product of an alkylphenol is a Group II metal salt.

3. The process of claim 1 wherein one of $R_1$ and $R_2$ is hydrogen and the other is hydrogen or methyl.

4. The process of claim 1 wherein the alkylene carbonate is ethylene carbonate.

5. The process of claim 1 further comprising recovering the product by filtering the reaction mixture to remove sediment.

6. The process of claim 1 wherein the alkylene carbonate is added to the reaction mixture over a time period for about 30 minutes to about 90 minutes.

7. A process for preparing Group II metal carbonated, overbased Mannich condensation products of alkylphenols which comprises the steps of:

(a) forming a reaction mixture by combining a Mannich condensation product of an alkylphenol wherein the alkyl group contains a sufficient number of carbon atoms to render oil-soluble the resulting Group II metal overbased Mannich alkylphenol, and one or more promoters, and a Group II metal oxide, hydroxide $C_1$-$C_6$ alkoxide; and (b) contacting said reaction mixture with an alkylene carbonate selected from ethylene carbonate or a mono-alkyl or di-alkyl substituted ethylene carbonate, said alkylene carbonate having the following structure:

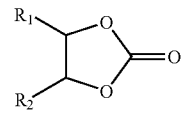

wherein $R_1$ and $R_2$ are independently hydrogen or alkyl containing one to three carbon atoms; and wherein the contacting is carried out for a time and at a temperature sufficient to form in situ carbon dioxide and alkylene glycol, to form a product comprising a Group II metal carbonated-overbased Mannich condensation product of an alkyphenol, wherein the promoter comprises a $C_2$-$C_{10}$ alkylene glycol, and a second promoter, which is different from the first promoter, comprises water, a $C_1$-$C_5$ mono- or di-alcohol, ethylene glycol or a mixture thereof, and wherein in step (b) the alkylene carbonate is added to the reaction mixture over a time period of about 15 minutes to about 120 minutes.

8. The process of claim 7 wherein the Mannich condensation product of an alkylphenol is a Group II metal salt.

9. The process of claim 7 wherein in step (b) the alkylene carbonate is added to the reaction mixture over a time period of about 30 minutes to about 90 minutes.

10. The process of claim 7 wherein in step (b) one of $R_1$ and $R_2$ is hydrogen and the other is hydrogen or methyl.

11. The process of claim 7 wherein in step (b) the alkylene carbonate is ethylene carbonate.

12. The process of claim 7 further comprising:

(c) recovering the product by filtering the reaction mixture of step (b) to remove sediment.

13. A process for preparing Group II metal carbonated, overbased Mannich condensation products of alkylphenols which comprises the steps of:

(a) forming a first reaction mixture by combining an alkylphenol wherein the alkyl group contains a sufficient number of carbon atoms to render oil-soluble the resulting Group II metal carbonated, overbased Mannich condensation products of alkylphenol with an aldehyde and an amine, in the presence of an inert hydrocarbon diluent;

(b) contacting said first reaction mixture with a second reaction mixture comprising a Group II metal oxide, hydroxide or $C_1$-$C_6$ alkoxide, and a promoter to form a third reaction mixture; and (c) contacting said third reaction mixture with an alkylene carbonate selected from ethylene carbonate or a mono-alkyl or di-alkyl substituted ethylene carbonate, said alkylene carbonate having the following structure:

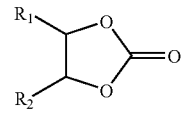

wherein $R_1$ and $R_2$ are independently hydrogen or alkyl containing one to three carbon atoms; and wherein said contacting is carried out for a time and at a temperature sufficient to form in situ carbon dioxide and alkylene glycol to form a product comprising a Group II metal carbonated, overbased Mannich condensation product of an alkylphenol.

14. The process of claim 13 wherein in step (c) the alkylene carbonate is added to the third reaction mixture over a time period of about 15 minutes to about 120 minutes.

15. The process of claim 14 wherein in step (c) the alkylene carbonate is added to the third reaction mixture over a time period of about 30 minutes to about 90 minutes.

16. The process of claim 13 wherein in step (c) one of $R_1$ and $R_2$ is hydrogen and the other is hydrogen or methyl.

17. The process of claim 13 wherein in step (c) the alkylene carbonate is ethylene carbonate.

18. The process of claim 13 wherein in step (b) the promoter is a $C_2$-$C_{10}$ alkylene glycol.

19. The process of claim 13 wherein step (a) further comprises a promoter, wherein the promoter comprises water, a $C_1$-$C_5$ mono- or di-alcohol, ethylene glycol or a mixture thereof.

20. The process of claim 13 wherein in step (a) the amine is an aliphatic amine, an aromatic amine, a polyfunctional amine or mixtures thereof, containing at least one amino group characterized by the presence of at least one active hydrogen or methylene group, and wherein the amine contains only primary amino groups, only secondary amino groups, or both primary and secondary amino groups.

21. The process of claim 20 wherein the aliphatic amine is an alkylene diamine, a dialkylamine, a polyalkylene polyamine or mixtures thereof.

22. The process of claim 20 wherein the aromatic amine is a single-ring aromatic amine, a double-ring aromatic amine or mixtures thereof.

23. The process of claim 13 wherein in step (a) the aldehyde is an aliphatic aldehyde, aromatic aldehyde, a heterocyclic aldehyde or mixtures thereof.

24. The process of claim 23 wherein the aliphatic aldehyde is formaldehyde or paraformaldehyde.

25. The process of claim 23 wherein the aromatic aldehyde is benzaldehyde.

26. The process of claim 23 wherein the heterocyclic aldehyde is furfural.

27. The process of claim 13 wherein the molar ratios of the alkylphenol, the aldehyde and the amine are from about 1:1.8:1 to about 1:3:1.

28. The process of claim 13 further comprising:
(d) recovering the product by filtering the third reaction mixture of step (c) to remove sediment.

29. The process of claim 13 wherein the alkyl group of the alkylphenol is a straight-chain alkyl group or branched-chain alkyl group containing at least 10 carbon atoms.

30. The process of claim 29 wherein the straight-chain alkyl group or the branched-chain alkyl group contains from about 12 carbon atoms to about 50 carbon atoms.

31. The process of claim 29 wherein the alkyl group of the alkylphenol contains from about 25 to about 100 mole percent straight-chain alkyl groups containing from about 15 to about 35 carbon atoms and from about 75 to about 0 mole percent branched-chain alkyl groups containing from at least 10 to about 18 carbon atoms.

32. The process of claim 31 wherein the alkyl group of the alkylphenol contains from about 40 to about 70 mole percent straight-chain alkyl groups containing from about 15 to about 35 carbon atoms and from about 60 to about 30 mole percent branched-chain alkyl groups containing from at least 10 to about 18 carbon atoms.

33. The process of claim 13 wherein the alkyl group of the alkylphenol is attached predominantly at the para position of the phenol ring.

34. The process of claim 33 wherein the alkylphenol containing the para attachment of the alkyl group is from about 70 to about 95 weight percent of the total alkylphenol.

35. The process of claim 13 wherein the Group II metal oxide, hydroxide or $C_1$-$C_6$ alkoxide is selected from the group consisting of calcium, barium, and magnesium oxide, hydroxide, $C_1$-$C_6$ alkoxide and mixtures thereof.

36. The process of claim 35 wherein the Group II metal oxide, hydroxide or $C_1$-$C_6$ alkoxide is calcium hydroxide.

\* \* \* \* \*